United States Patent [19]

Behnk

[11] Patent Number: 5,238,854
[45] Date of Patent: Aug. 24, 1993

[54] METHOD FOR TESTING AND MEASURING BLOOD CLOTTING TIME

[76] Inventor: Holger Behnk, Holitzberg 61, D-2000 Hamburg 62, Fed. Rep. of Germany

[21] Appl. No.: 428,358

[22] Filed: Oct. 27, 1989

[30] Foreign Application Priority Data

Oct. 31, 1988 [DE] Fed. Rep. of Germany ....... 3837078

[51] Int. Cl.$^5$ .......................................... G01N 33/86
[52] U.S. Cl. ...................................... 436/69; 435/13; 436/165
[58] Field of Search ................... 436/69, 165; 435/13

[56] References Cited

U.S. PATENT DOCUMENTS

| | | |
|---|---|---|
| 3,233,975 | 2/1966 | McCormick . |
| 3,504,376 | 3/1970 | Bednar et al. . |
| 4,043,673 | 8/1977 | Farrell et al. ........................ 436/165 |
| 4,081,242 | 3/1978 | Girolami ................................ 436/69 |
| 4,357,301 | 11/1982 | Cassaday et al. .................... 422/102 |
| 4,371,498 | 2/1983 | Scordato et al. .................... 422/102 |
| 4,497,774 | 2/1985 | Scordato ............................... 436/69 |
| 4,659,550 | 4/1987 | Schildknechk ....................... 435/13 |
| 4,876,069 | 10/1989 | Jochimsen ............................ 436/69 |
| 4,963,498 | 10/1990 | Hillman et al. ...................... 436/69 |

FOREIGN PATENT DOCUMENTS 2383444 10/1978 France .
8702131 4/1987 World Int. Prop. O. .

*Primary Examiner*—Robert J. Hill, Jr.
*Attorney, Agent, or Firm*—Chilton, Alix & Van Kirk

[57] ABSTRACT

The method and the apparatus serve for testing and measuring blood clotting time. Blood or blood plasma (12) and a reagent (13) are introduced into a measuring cuvette (8). The clotting time is measured electrooptically with the aid of a stirring element (9) which is arranged in the measuring cuvette (8), can be attracted magnetically and is driven by a magnetic stirring device arranged outside the measuring cuvette (8). The method and apparatus are suitable for automatic measuring methods owing to the fact that blood plasma (12) and reagent (13) are introduced beside one another onto an essentially horizontal internal surface (10) of a measuring cuvette (8) provided with an opening above this surface (10), in that the measuring cuvette (8) and its contents are heated to the reaction temperature (step 7), in that the measuring cuvette is pivoted by essentially 90° in such a way that the internal surface (10) stands essentially perpendicular and plasma (12) and reagent (13) flow together, and in that the measurement is subsequently carried out.

23 Claims, 4 Drawing Sheets

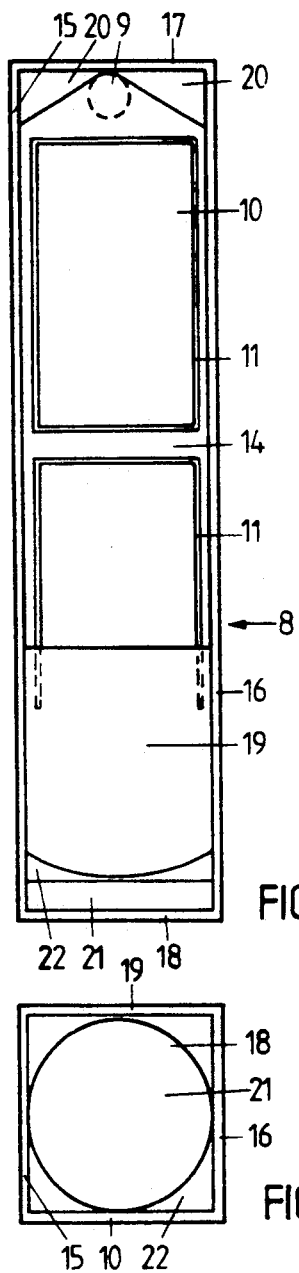
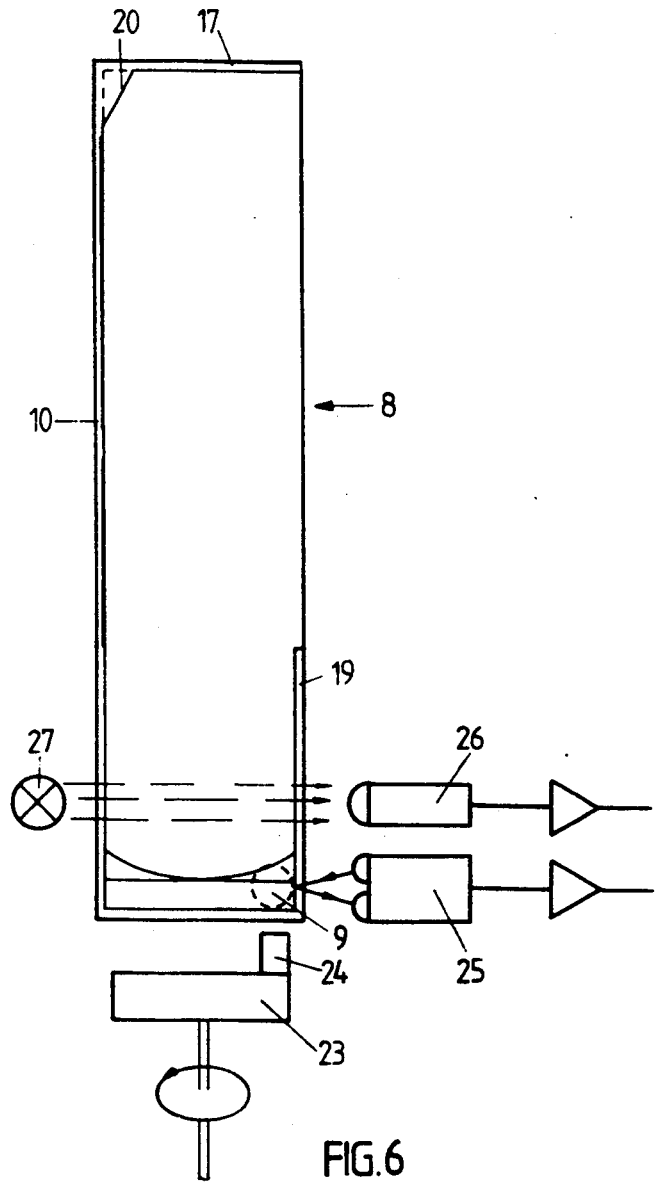
FIG.4
FIG.5
FIG.6

METHOD FOR TESTING AND MEASURING BLOOD CLOTTING TIME

BACKGROUND AND SUMMARY OF THE INVENTION

The invention concerns a method and an apparatus for testing and measuring blood clotting time, in which blood or blood plasma and a reagent are introduced into a measuring cuvette and the clotting time is measured electro-optically with the aid of a stirring element which is arranged in the measuring cuvette, can be attracted magnetically and is driven by a magnetic stirring device arranged outside the measuring cuvette.

Methods and apparatuses of this type (DE-PS 3,127,560, EP-PS 0,090,192) permit very multifarious and dissimilar types of blood clotting time measurement. Although very accurate values are obtained, the costs of operation by trained personnel are necessarily high.

Although automatic methods for measuring blood clotting time are known, they cannot, however, be used for the measuring method with stirring elements mentioned at the beginning. Moreover, these methods have grave disadvantages. These disadvantages are connected with the fact that, on the one hand, the blood plasma and the reagents must be cooled before the measurement, whereas, on the other hand, the measurement must take place at a temperature which may have only very small deviations from 37° C. If the reagents are not kept at a temperature of 15° C., they partially decompose even after half an hour. On the other hand, if the temperature departs during measurement by only 1° from 37° C., there is already a measurement error of 10%.

In an automatic method for testing and measuring blood clotting time (brochure MLA Electra 800 from AHS/Deutschland GmbH), the measuring cuvettes, which have previously been filled with blood plasma by hand, are inserted into a carousel in which their temperature is controlled. When the cuvette is located at the appropriate station, the reagent is then filled into it by a pump from the cooled storage vessel through a plate-shaped element in which heating to 37° C. takes place. The plasma, which has been heated to 37° C., and the likewise heated reagent then meet here. The disadvantage consists, for one thing, in that the plasma still has to be filled into the measuring cuvettes by hand, and in that these measuring cuvettes then need to be inserted by hand into the carousel. A further disadvantage consists in that the plate-shaped heat exchangers take up a relatively high amount of reagent. When measurement is interrupted, it is then necessary for the reagent to be pumped back from these plate-shaped heat exchangers, since otherwise it decomposes. However, residual amounts subsequently dry on the walls, so that when restarting there is the danger of blockages or erroneous measurements. Consequently, the heat exchanger plates must be frequently replaced. Further, there is the danger of losses of relatively expensive reagent liquid. Moreover, a separate pump and a separate heat exchange surface are required for each reagent, so that with the named apparatus it is possible simultaneously to use only two reagents for one measurement. This number of reagents cannot be increased ad lib without excessive expenditure.

In a further method (brochure COAC-A-Mater-X2 from the firm Labordiagnostica Gödecke) the plate-shaped heat exchangers are dispensed with. Instead of these, the hoses for the reagents are lead through a plate-shaped element, which is at a temperature of 37° C. Here, after measurement has been interrupted the hoses can and/or must be cleaned or replaced, and this is likewise troublesome and expensive; there is also a high risk of erroneous measurements.

In a further previously known method (brochure ACL Automated Coagulation Laboratory from Instrumentation Laboratory), the plasma is automatically introduced into a cuvettes from a centrifuge tube. The reagents are also filled into the measuring cuvette automatically from cooled storage vessels In this process, the transfer device can also be fed intermittently to a washing device. Subsequently, the space with the measuring cuvettes arranged on a centrifuge is closed off. The measuring cuvettes are then heated, and upon reaching a temperature of 37° C. are set into rapid rotation resulting in thorough mixing due to the centrifuge effect. This system likewise has various disadvantages.

For one thing, not all types of measurements are possible in the centrifuge. It is not possible to use any reagents which sediment, e.g. PTT reagent with kaolin. Again, the advantageous measurements with stirring elements are not possible. Moreover, the cuvettes must be absolutely leakproof, since otherwise at the high centrifuging rate of 1200 rpm liquid penetrates into the rotor space and contaminates it, and especially also contaminates the measuring devices. Finally, the measuring cuvettes cannot be removed automatically after the measurement, but must be taken out by hand.

The object of the invention consists in creating a method of the type mentioned at the beginning in which it is possible, by exploiting the advantages of the method with a stirring element, to conduct very many different tests with various reagents, changing rapidly from one reagent to another, the method being designed especially for automatic applications.

The object is achieved according to the invention in that blood plasma and reagent are introduced beside one another onto an essentially horizontal internal surface of a measuring cuvette provided with an opening above this surface, in that the measuring cuvette and its contents are heated to the reaction temperature, in that the measuring cuvette is pivoted in the measuring station by essentially 90° in such a way that the internal surface stands essentially perpendicular and plasma and reagent flow together, and in that the measurement is subsequently carried out.

DETAILED DESCRIPTION OF THE INVENTION

Thus, blood plasma and reagent are brought beside one another onto an essentially horizontal surface; in this connection, they are still initially at a temperature of, e.g., 15° C., at which no reactions yet take place. Subsequently, the measuring cuvette and its contents are then heated to the reaction temperature, although no reactions yet take place between plasma and reagent, since the two liquids are arranged beside one another and have not yet been mixed with one another. Subsequently, the measuring cuvette is then pivoted by essentially 90° in such a way that the internal surface stands essentially perpendicular, whereby plasma and reagent flow together. Subsequently, the measurement can then be carried out.

In this connection, the measuring cuvettes can be filled automatically with plasma and reagents, using only one pump. Problems of any sort concerning contamination, incubation or decomposition and the like do not arise, since the pumps and the feeder devices can be cooled. The measuring cuvette can then be conducted automatically into a heating station, where it is heated until it has reached a temperature of 37° C. The measurement can then subsequently be carried out, and in the process the advantages of the method with a stirring element can be exploited. Automatic removal then subsequently takes place. However, it is also possible, of course, to carry out the method by hand, if an appropriate apparatus for carrying out the method automatically is not available.

If the internal surface is initially inclined by a few degrees so that the end region of the internal surface, which is to be pivoted upwards during pivoting, lies deeper than the remaining regions of the internal surface, the stirring element can initially be arranged in this deeper region. In this process, it is possible for the cuvette to be initially inclined, and then for the stirring element to be introduced into the deeper lying region, or else for the stirring element to be introduced only so that it rolls to the desired position when the inclination is subsequently carried out. At the start of the pivoting process, the stirring element then falls into the reagent, and then into the plasma, and draws the latter downwards with it, the result being that a better mixing through is already achieved at the beginning. At the same time, the stirring element ensures a constant speed during transport of the reagent.

In other embodiments, the inclination will be chosen in precisely the opposite sense, so that when pivoting is carried out, the stirring element does not fall through the liquids, which could lead to splashes and undesired distribution of the liquids.

It has turned out to be especially advantageous if the stirring element is a metal ball.

If, after being pivoted, the measuring cuvette is dropped through a limited distance and strikes a stop face, the stirring element and the liquids are moved downwards impulsively, so that maximum amounts of the liquids are rapidly available here and can be mixed through.

It is possible without any difficulty to design the method like an assembly line in such a way that a plurality of measuring cuvettes are simultaneously conducted through the individual stations consecutively in sequence, and are subsequently removed.

A measuring cuvette for carrying out the method is characterized in that the internal surface for accepting plasma and reagent is essentially flat and is provided with surface structures preventing the liquids from flowing together. Because the internal surface is essentially flat, especially large amounts of plasma and reagent can be arranged beside one another but are prevented by the surface structures from flowing together already in this position of the measuring cuvette. If the measuring cuvette is subsequently pivoted, especially by approximately 95°, so that it subsequently stands perpendicular, these surface structures can no longer prevent a flowing together. This holds true especially if, after being pivoted, the cuvette is also dropped onto a stop face, a travel distance of 5 mm already being sufficient in this regard.

The surface structures can be small trough-like indentations for the liquids.

It is expedient for the surface structures to enclose regions separated from one another by an interface. In this connection, the liquids initially remain in the surface regions, and are separated from one another by the interface. The surface structures can be linear, ridge-like projections. However, the surface structures are especially simple to produce if they are linear notches.

If, in the immediately deeper-lying region, the internal surface is bounded at its rim by two boundary walls running together in the middle at an obtuse angle, a spherical stirring element will initially automatically roll into the middle of the edge, so that it then falls from this middle through the drops of liquid, and thereby carries along an especially large amount of liquids into the region in which the subsequent measurement is to be carried out. It is expedient to provide a central, cylindrical indentation on the surface on which the stirring element and the liquid meet, so that here the spherical stirring element can execute a circular movement, which is effected by the magnetic stirring device.

It is expedient to provide that the rim regions arranged outside the cylindrical recess are bevelled inwards, and in the position after the pivoting are bevelled downwards, these end regions having at least partially a smaller thickness than the diameter of the ball. These bevelled, especially spherical shell-shaped bevelled regions, ensure that the ball also rapidly reaches the predetermined cylindrical path even if it strikes the rim regions. If the end regions have a smaller thickness than the diameter of the ball, it is not only the liquid material in the cylindrical region which is stirred through by the ball; rather, a stirring effect is also exerted on the liquid portions located in the rim regions, especially in the corners of a rectangular measuring cuvette.

As already mentioned, the method and the apparatus have the advantage that it is possible to conduct very many different measurements simultaneously, to be precise a total of up to 13 determinations. It is easily possibly for the corresponding 13 reagents to be stored cooled, and for a complete clotting status to be made at any time. Whereas with the previously known automatic apparatuses there were three pumps, e.g. for the basic determinations of PT (prothrombin time) and PTT (partial thromboplastin time) which have sufficed for the clotting status for a long time, it is now also possible, in addition, to measure TT (thrombin time) and fibrinogen which already happens in many hospitals. It is not possible to measure this for each patient in one pass using any previously known apparatus. If errors should arise in the case of this clotting status, it is, in addition, possible and necessary for the factors to be measured as well. This then adds up to the total of 13 determinations mentioned above.

If a plurality of measuring cuvettes are arranged in a common holder which has a toothed rack, this plurality of measuring cuvettes can be conducted through the various stations by a gear drive. In this way, a large number of tests can be carried out in a rapid sequence in a very rational way.

BRIEF DESCRIPTION OF THE DRAWINGS

The invention is described on the basis of an exemplary embodiment with reference to the attached drawings, in which:

FIG. 4 shows a top view of the measuring cuvette in a prone state;

FIG. 5 shows an end view of the same measuring cuvette;

FIG. 6 shows the measuring cuvette in the measuring station, the measuring cuvette being shown rotated about its longitudinal axis by 90° with respect to the representation of FIG. 4.

Figure 1:
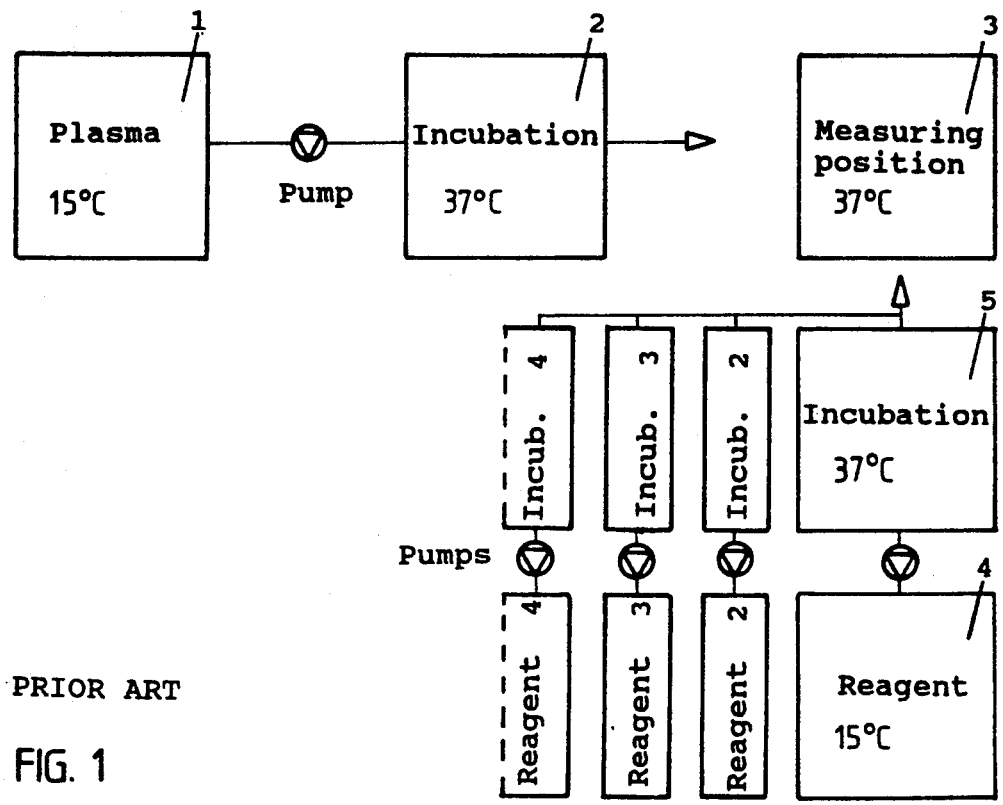
FIG. 1 shows the block diagram of a previously known automatic method.

In the block diagram of the previously known method of FIG. 1, the plasma is firstly kept at a temperature of 15° C. in step 1. Incubation to 37° C. then takes place in step 2 via surface contact with the incubator. Subsequently, the plasma thus heated is then fed to the measuring station 3. On the other hand, the reagent is firstly kept in a station 4 at a temperature of 15° C. Incubation to 37° C. then takes place in station 5 in plate-shaped heat exchangers or in the hoses. Subsequently, the reagent is then also brought into the measuring position 3.

Thus, in the case of automation one pump is required for plasma and reagent in step 1. In step 3 one pump is required for each reagent, and also a heat exchanger.

Figure 2:
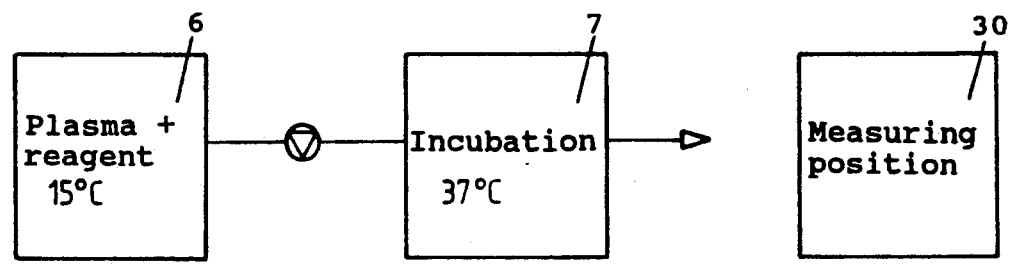
FIG. 2 shows the block diagram of the method according to the invention.

By contrast, the method according to the invention, which is represented in FIG. 2, is substantially simpler. Here, plasma and reagent are introduced beside one another into the measuring cuvette in step 6 at a temperature of 15° C. Subsequently, incubation to a temperature of 37° C. takes place in step 7. After the measuring cuvette has been pivoted, measurement then takes place in the measuring position 30. In the case of automation only one pump is required for plasma and reagent in step 6.

Figure 3:
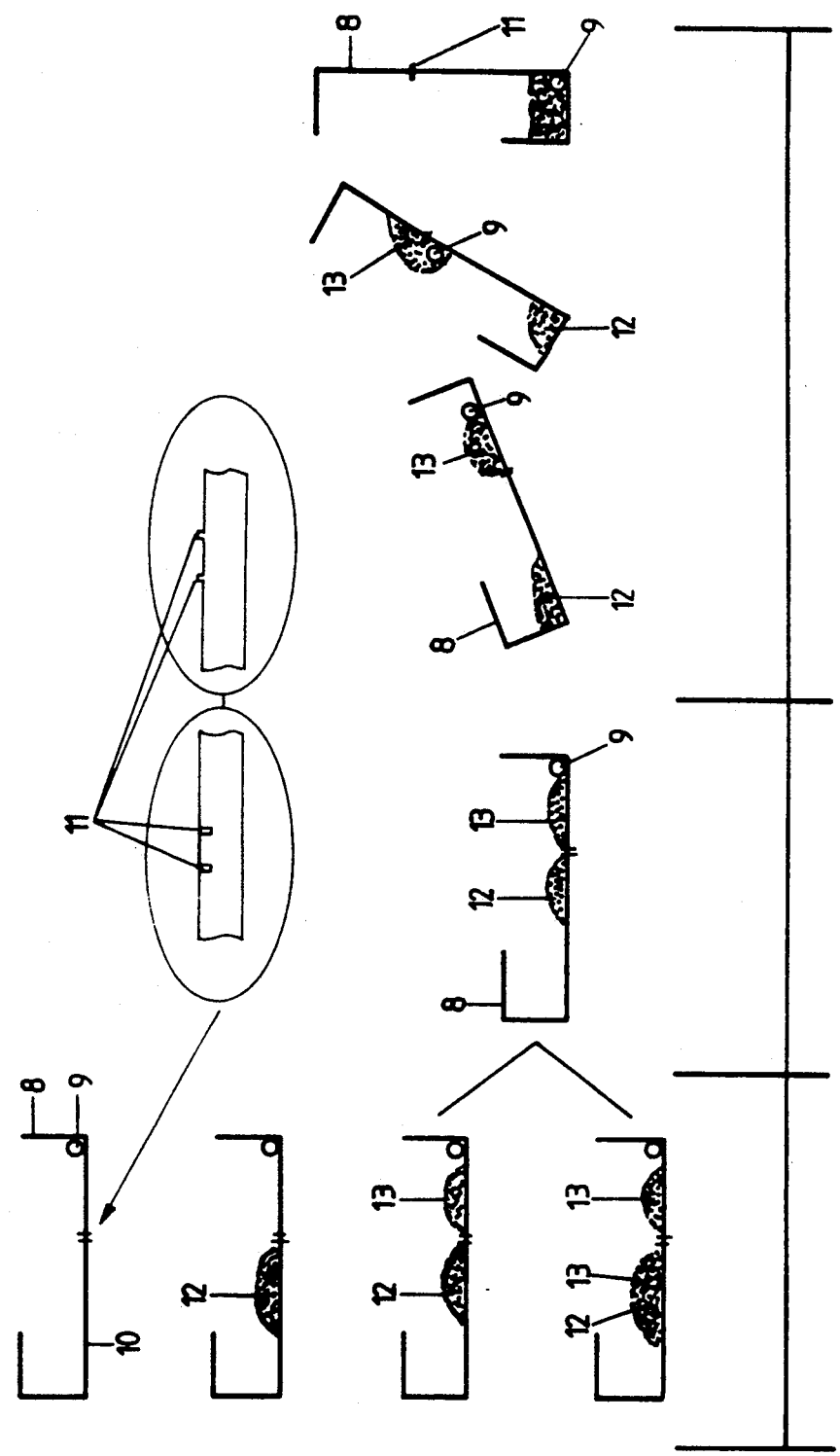
FIG. 3 shows the principle of the use of the measuring cuvette according to the invention.

The process according to the invention is shown more clearly in FIG. 3, which shows a side view in section of the measuring cuvette 8.

The measuring cuvette 8 is essentially in the shape of a parallelepiped, and has an opening on one of its faces, which occupies the main part of these faces. The measuring cuvette 8 thus has a shoe-like shape. In step 6, the stirring element 9 is first introduced in the form of a ball. In this process, the measuring cuvette is a little inclined, namely in such a way that the ball 9 is located at the lowest position. This inclination of the cuvette 8 is not absolutely necessary, and is also not shown in FIG. 3. In the middle, the lower surface 10 of the cuvette 8 is subdivided by scribed indentations 11 or ridge-like projections, which will be described further in more detail in connection with FIG. 4. These indentations or projections 11 are also shown further magnified in FIG. 3. The plasma 12 is introduced to the left of these scribings 11. Subsequently, a reagent 13 is introduced to the right of the plasma 12 and the scribings 11 (from above to below in the representation of FIG. 3). If it is necessary, a further reagent can still subsequently be fed to the plasma 12.

The measuring cuvette 8 is brought in this condition into a further station, and incubated in step 7 to a temperature of 37° C. When the desired temperature has been reached, the cuvette 8 is then tilted in step 3, i.e. in the measuring station. As may be seen in the middle portion in the case of step 3, in this process the ball 9 penetrates into the reagent 13 and carries it along, so that in the right-hand position the ball 9 is located below, and plasma 12 and reagent 13 are thereby mixed. The clotting time is then measured here.

The cuvette 8 is shown more clearly in a top view in FIG. 4. The lower surface 10 in the position of steps 6 and 7 of FIG. 3, onto which plasma 12 and reagent 13 are brought, is provided with mutually orthogonal notches, which border a closed area at least in the upper region in FIG. 4. The two regions, which are bordered at least partially by the notches 11, are separated by an intermediate region 14, so that the liquids whose flow is prevented by the notches 11, are clearly separated from one another, as long as the measuring cuvette 8 occupies its essentially horizontal position.

The side walls 15 and 16 are closed—as are the end faces 17 and 18. A portion of the upper face is closed off by a cover 19.

At the top in FIG. 4, the base face 10 is bounded by sloping faces 20, so that the ball 9 is arranged in the middle of face 10 if the cuvette 8 is inclined somewhat deeper in this region. The end face 18 lying opposite has a cylindrical recess 21, the rim regions 22 being bevelled at the corners, as may also be seen from FIG. 4 In this connection, FIG. 5 is a top view of the end face 18.

Owing to the sloping faces 22, the ball falls into the cylindrical recess 21 when the measuring cuvette 8 is pivoted into the vertical position in FIG. 6. In this process, the ball 9 projects into the space above the cylindrical recess 21, so that it thoroughly mixes the liquid located in the lower region after the pivoting, when it is moved by a magnetic stirrer 23 with a permanent magnet 24.

The start of clotting can be determined by photoelectric devices, which are represented diagrammatically by 25 and 26. In this connection, the device 25 is a reflection measurement while the device 26 with a light source 27 is a transmission measuring device. These measuring devices are known from the patents named at the beginning, so that it is not necessary to describe them in more detail here. Obviously, the measuring cuvette is transparent, in order that the measurements can be carried out.

Figure 7:
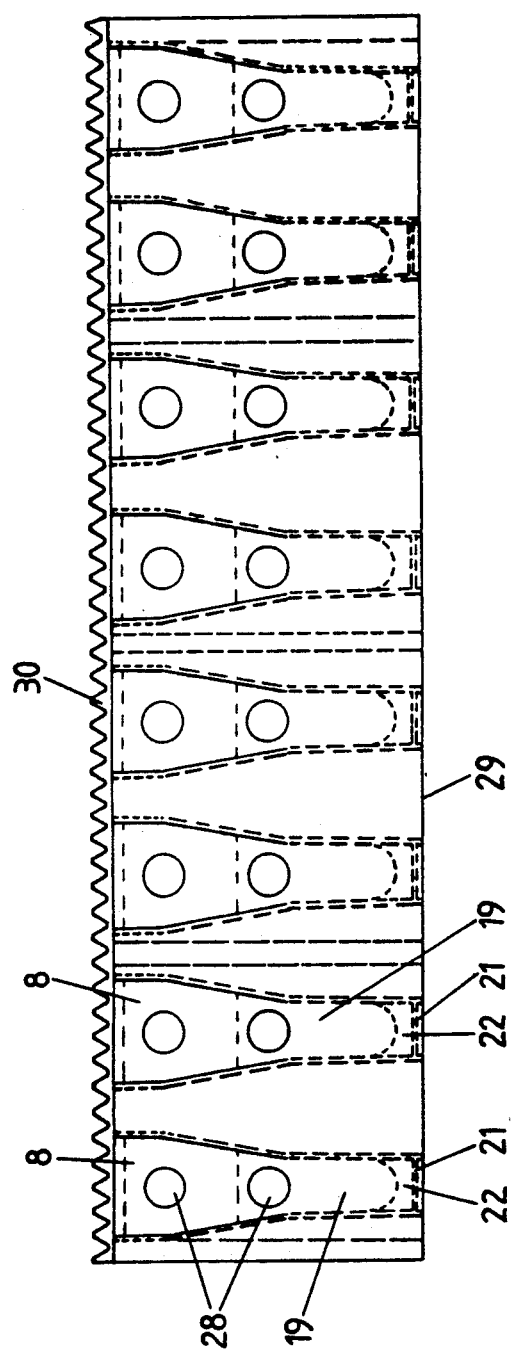
FIG. 7 shows a number of measuring cuvettes, which are grouped in a common holder with a toothed rack.

It is shown in FIG. 7 that a series of measuring cuvettes 8 are arranged beside one another in a holder 29, which carries a toothed rack 30 on its outside. The holder can be transported with the measuring cuvettes through the individual stations with the aid of this toothed rack 30 and of a gear drive (not shown), so that a large number of tests can be carried out in rapid sequence. In the embodiment shown in FIG. 7, the cover plate 19 also covers more or less the whole region of the measuring cuvette 8; the cover plate 19 has only two openings 28, through which plasma, reagent and ball can be put in.

I claim:

1. Method of testing and measuring blood clotting time, comprising steps in which a reagent and one of blood and blood plasma are introduced into at least one measuring cuvette and the clotting time is measured electro-optically with the aid of a stirring element which is arranged in the at least one measuring cuvette, can be attracted magnetically and is driven by a magnetic stirring device arranged outside the at least one measuring cuvette, wherein the reagent and the one of blood and blood plasma are introduced beside one another in an unmixed arrangement on a surface of the at least one measuring cuvette which is positioned within a few degrees of a horizontal plane and is provided with an opening above the surface, the at least one measuring cuvette and its contents are heated to a temperature sufficient to induce reaction, the at least one measuring cuvette is pivoted in a measuring position by essentially 90° in such a way that the surface is generally vertical and the one of blood and blood plasma and reagent flow together, and wherein the clotting time measurement is subsequently carried out.

2. Method according to claim 1, wherein a metal ball is used as the stirring element.

3. Method according to claim 1, wherein after being pivoted the at least one measuring cuvette is dropped through a limited distance and strikes a stop face.

4. Method according to claim 1 wherein the method proceeds automatically and the at least one measuring cuvette is conducted through a filling station for introducing the reagent and the one of blood and blood plasma, a heating station and a measuring station to a removal station.

5. Method according to claim 4, wherein a plurality of measuring cuvettes are conducted through the stations in rapid sequence.

6. A method of determining the clotting time of one of blood and blood plasma comprising the steps of:
   introducing the one of blood and blood plasma and a reagent to a first internal surface of a measuring cuvette beside one another in an unmixed arrangement, the first internal surface of the cuvette being positioned within several degrees of a horizontal plane,
   mixing the one of blood and blood plasma and reagent by rotating the cuvette in a vertical direction to an angle sufficient to induce mixing and stirring the one of blood and blood plasma and reagent using a stirring element which is disposed within the cuvette, can be attracted magnetically, and is driven by a magnetic stirring device disposed outside the cuvette, and
   subsequently measuring the clotting time of the one of blood and blood plasma.

7. A method according to claim 6, wherein after introducing the one of blood and blood plasma to the cuvette and before mixing the one of blood and blood plasma and reagent, the one of blood and blood plasma and reagent are heated to a temperature sufficient to induce reaction upon mixing, and after mixing, the clotting time of the one of blood and blood plasma is measured.

8. A method according to claim 7, wherein the mixing step includes dropping the cuvette a limited distance onto a stop face after rotation.

9. A method according to claim 7, wherein the steps of introducing, heating, mixing and measuring are automated.

10. A method according to claim 7, wherein the one of blood and blood plasma is blood plasma.

11. A method according to claim 7, wherein the step of introducing the one of blood and blood plasma and reagent to the cuvette in an unmixed arrangement includes introducing the one of blood and blood plasma on one side of a notch or projection on the first internal surface of the cuvette and introducing the reagent on another side of the notch or projection.

12. A method according to claim 7, wherein the step of introducing the one of blood and blood plasma and reagent to the cuvette in an unmixed arrangement includes introducing the one of blood and blood plasma on one side of a first notch or projection on the first internal surface of the cuvette and introducing the reagent on one side of a second notch or projection that is not adjacent to the first notch or projection.

13. A method according to claim 6, wherein, before the mixing step, the first internal surface of the cuvette is inclined relative to a horizontal plane in an amount sufficient to cause the stirring element to be gravitationally positioned adjacent one of a first end portion and an opposite, laterally spaced second end portion of the cuvette.

14. A method according to claim 13, wherein, before the mixing step, the stirring element is disposed at the first end portion of the cuvette.

15. A method according to claim 14, wherein, during the mixing step, the first end portion of the cuvette is rotated upward at least about 90°.

16. A method according to claim 15, wherein, before mixing, the reagent is disposed near the first end portion of the cuvette.

17. A method according to claim 6, wherein the stirring element is a metal ball.

18. A method according to claim 6, wherein the steps of introducing, mixing and measuring are automated.

19. A method according to claim 6, wherein the cuvette is one of a plurality of cuvettes, and the steps of introducing, mixing and measuring are conducted substantially concurrently in each of the plurality of cuvettes.

20. A method according to claim 6, wherein the step of mixing the one of blood and blood plasma and reagent by rotating the cuvette includes positioning the stirring element at the center of a first inner boundary wall that is substantially perpendicular to the first internal surface and causing the stirring element to fall from the center of the first inner boundary wall.

21. A method according to claim 6, wherein the step of mixing includes moving the stirring element in a circular direction.

22. A method according to claim 6, wherein the step of introducing the one of blood and blood plasma to the first internal surface of the measuring cuvette includes inserting the one of blood and blood plasma through an opening in the cuvette above the first internal surface.

23. A method of determining the clotting time of one of blood and blood plasma, comprising the steps of:
   introducing one of blood and blood plasma and a reagent to a substantially flat first internal surface of a measuring cuvette beside one another in an unmixed arrangement, the cuvette having a stirring element movably disposed therein, and having a first end portion and an opposite second end portion, the second end portion being inclined relative to a horizontal plane and relative to the first end portion in an amount sufficient to cause the stirring element to lie adjacent the first end portion, the one of blood and blood plasma and reagent being maintained in an unmixed arrangement by at least one notch or projection on the first internal surface of the cuvette,
   heating the one of blood and blood plasma and reagent to a temperature sufficient to induce reaction upon mixing,
   mixing the one of blood and blood plasma and reagent by rotating the cuvette in a vertical direction to an angle sufficient to induce mixing and to cause the stirring element to fall from the first end portion of the cuvette to the second end portion, and
   subsequently measuring the clotting time of the one of blood and blood plasma in the cuvette.

* * * * *